(12) United States Patent
Marciano et al.

(10) Patent No.: US 11,309,062 B2
(45) Date of Patent: Apr. 19, 2022

(54) HIERARCHICAL OPTIMIZED DETECTION OF RELATIVES

(71) Applicants: Michael Marciano, Manlius, NY (US); Jonathan D. Adelman, Mexico, NY (US)

(72) Inventors: Michael Marciano, Manlius, NY (US); Jonathan D. Adelman, Mexico, NY (US)

(73) Assignee: Syracuse University, Syracuse, NY (US)

( * ) Notice: Subject to any disclaimer, the term of this patent is extended or adjusted under 35 U.S.C. 154(b) by 765 days.

(21) Appl. No.: 16/148,341

(22) Filed: Oct. 1, 2018

(65) Prior Publication Data

US 2019/0102517 A1   Apr. 4, 2019

Related U.S. Application Data

(60) Provisional application No. 62/566,502, filed on Oct. 1, 2017.

(51) Int. Cl.
*G16B 40/00* (2019.01)
*G16B 30/00* (2019.01)
*G16B 20/20* (2019.01)
*G16H 10/20* (2018.01)
*C12Q 1/68* (2018.01)

(52) U.S. Cl.
CPC .............. *G16B 40/00* (2019.02); *G16B 20/20* (2019.02); *G16B 30/00* (2019.02); *C12Q 1/68* (2013.01); *G16H 10/20* (2018.01)

(58) Field of Classification Search
CPC ......... G16B 40/00; G16B 20/20; G16B 30/00
USPC .......................................................... 702/19
See application file for complete search history.

*Primary Examiner* — Jerry Lin
(74) *Attorney, Agent, or Firm* — Bond Schoeneck and King PLLC; David Nocilly

(57) ABSTRACT

A system for evaluating a DNA sample and determining whether the sample contains related individuals and/or unrelated individuals with high levels of alleles sharing. Trained and pre-validated machine learning algorithms are to rapidly and probabilistically assess the presence of relatives in a DNA mixture. To make a probabilistic determination, the system evaluates aspect of the sample that have not be considered before, such as peak heights, peak height ratios, maximum peak heights, minimum peak heights, ratios of allele heights to one another, number of contributors using maximum allele count method, and quantitative measures of the amount of DNA contributed by the male and female organisms. The system identifies whether a DNA sample has contributors that are not readily identifiable based on the data and can thus improve downstream analysis.

18 Claims, 4 Drawing Sheets

| sample | DNA Marker (Locus) | prob_allele sharing class_0 | prob_allele sharing class_1 | prob_allele sharing class_2 | prob_allele sharing class_3 | prob_allele sharing class_4 | prob_allele sharing class_5 | prob_allele sharing class_6 |
|---|---|---|---|---|---|---|---|---|
| Sample 1 | A | 0.011953 | 0.005893 | 0.940686 | 0.013658 | 0.014537 | 0.010854 | 0.002419 |
| Sample 1 | B | 0.010702 | 0.005886 | 0.942263 | 0.013572 | 0.014322 | 0.010839 | 0.002416 |
| Sample 1 | C | 0.010742 | 0.005887 | 0.942027 | 0.013635 | 0.014402 | 0.010891 | 0.002417 |
| Sample 1 | D | 0.935756 | 0.00577 | 0.018155 | 0.013306 | 0.014022 | 0.01062 | 0.00237 |
| Sample 2 | A | 0.011028 | 0.017034 | 0.928087 | 0.015514 | 0.014747 | 0.011113 | 0.002477 |
| Sample 2 | B | 0.012547 | 0.406949 | 0.51751 | 0.030543 | 0.016772 | 0.012881 | 0.002798 |
| Sample 2 | C | 0.010674 | 0.005862 | 0.017191 | 0.032584 | 0.036736 | 0.893352 | 0.0036 |
| Sample 2 | D | 0.010885 | 0.005993 | 0.019385 | 0.541781 | 0.408416 | 0.011095 | 0.002445 |

FIG. 1

| sample | Probability relatives in sample |
|---|---|
| Sample 1 | 0.002181522 |
| Sample 2 | 0.991190644 |
| Sample 3 | 0.003399336 |

FIG. 2

| No. | Sample | Invention Used? | Expected number of contributors | estimated number of contributors | prob_NOC_1 | prob_NOC_2 | prob_NOC_3 | prob_NOC_4 | Fold improvement | Percent improvement |
|---|---|---|---|---|---|---|---|---|---|---|
| 1 | Family 1 -Mother,Father,Sibling 2 | Y | 3 | 2 | 0 | 0.551122606 | 0.406441918 | 0.042435475 | 1.5 | 13.1% |
|  |  |  | 3 | 2 | 0 | 0.691136858 | 0.275735192 | 0.033127795 |  |  |
| 2 | Family 1 -Mother,Father,Sibling 1,Sibling 2 | Y | 3 | 2 | 0 | 0.911346907 | 0.088226439 | 0.000426654 | 0.6 | 6.6% |
|  |  |  | 3 | 2 | 0 | 0.842547686 | 0.154766 | 0.002775714 |  |  |
| 3 | Family 2 -Mother,Sibling 1 | Y | 2 | 2 | 0.037656515 | 0.962343485 | 0 | 0 | 1.9 | 46.7% |
|  |  |  | 2 | 2 | 0.478049885 | 0.494900439 | 0.027049676 | 0 |  |  |
| 4 | Family 2 -Father,Sibling 1 | Y | 2 | 2 | 0 | 0.954660978 | 0.045269006 | 6.12143E-05 | 1 | 0.5% |
|  |  |  | 2 | 2 | 0 | 0.959739296 | 0.032063205 | 0.008197498 |  |  |
| 5 | Family 2 -Mother,Sibling 1,Sibling 2 | Y | 3 | 2 | 0 | 0.956735397 | 0.042690814 | 0.000573789 | 0.6 | 2.6% |
|  |  |  | 3 | 2 | 0 | 0.929559176 | 0.069124137 | 0.001316687 |  |  |
| 6 | Family 2 -Mother,Father,Sibling 2 | Y | 3 | 2 | 0 | 0.859153668 | 0.140846332 | 0 | 3.5 | 10.0% |
|  |  |  | 3 | 2 | 0 | 0.959376382 | 0.040623618 | 0 |  |  |
| 7 | Family 3 -Father,Sibling 1 | Y | 2 | 1 | 0.957234556 | 0.042765444 | 0 | 0 | 212.3 | 4.3% |
|  |  |  | 2 | 1 | 0.999798528 | 0.000201472 | 0 | 0 |  |  |
| 8 | Family 3 -Mother,Father,Sibling 2 | Y | 3 | 2 | 0 | 0.794090815 | 0.205587482 | 3.43654E-05 | 1 | 0.9% |
|  |  |  | 3 | 2 | 0 | 0.803028195 | 0.196971805 | 0 |  |  |
| 9 | Family 3 -Mother,Sibling 1,Sibling 2 | Y | 3 | 2 | 0 | 0.948737381 | 0.051262619 | 0 | 1.1 | 0.4% |
|  |  |  | 3 | 2 | 0 | 0.952942359 | 0.047057641 | 0 |  |  |
| 10 | Family 4 -Sibling 1,Sibling 2 | Y | 2 | 2 | 0 | 0.995819807 | 0.004145682 | 3.45113E-05 | 1.2 | 13.3% |
|  |  |  | 2 | 2 | 0.000130806 | 0.862358523 | 0.136743773 | 0.000766898 |  |  |
| 11 | Family 4 -Father,Sibling 1,Sibling 2 | Y | 3 | 2 | 0 | 0.557242653 | 0.439728069 | 0.003029278 | 1 | 1.1% |
|  |  |  | 3 | 2 | 0 | 0.520265771 | 0.428433596 | 0.051300633 |  |  |
| 12 | Family 5 -Father,Sibling 1 | Y | 2 | 1 | 0.49242942 | 0.279045962 | 0.184404081 | 0.044119808 | 1.3 | 7.2% |
|  |  |  | 2 | 1 | 0.694638695 | 0.206959862 | 0.015296989 | 0.083104454 |  |  |
| 13 | Family 5 -Mother,Sibling 1,Sibling 2 | Y | 3 | 2 | 0 | 0.65029881 | 0.349811709 | 0.000789481 | 2.8 | 22.6% |
|  |  |  | 3 | 2 | 0 | 0.861710279 | 0.122852745 | 0.015436975 |  |  |
| 14 | Family 6- Sibling 1, Sibling 2, Sibling 3, unrelated individual | Y | 4 | 2 | 0 | 0.66271193 | 0.274734066 | 0.062554004 | 1.2 | 1.1% |
|  |  |  | 4 | 2 | 0 | 0.740335465 | 0.207882192 | 0.051782343 |  |  |

FIG. 4

HIERARCHICAL OPTIMIZED DETECTION OF RELATIVES

CROSS-REFERENCE TO RELATED APPLICATIONS

The present application claims priority to U.S. Provisional Application No. 62/566,502, filed on Oct. 1, 2017.

BACKGROUND OF THE INVENTION

1. Field of the Invention

The present invention relates to allele sharing detection systems and, more particularly, to the probabilistically evaluation of a DNA mixture to determine whether the sample includes relatives and/or high levels of allele sharing.

2. Description of the Related Art

At the core of the genetic identification field, particularly in regard to forensic applications and clinical/medical research, is the challenge of DNA mixture interpretation. A common problem when analyzing DNA mixtures is identifying the presence of related contributors or contributors with high levels of allele sharing. Predicting the presence of DNA mixtures containing relatives is of critical importance to the forensic DNA field, in particular, where the inability to correctly identify challenging samples with relatives limits whether forensic samples can even be analyzed. This value extends to any discipline in which mixtures of DNA are present. Currently, there are no systems of methods for providing a probability that a particular sample includes contributors having a high degree of allele sharing and the analysis of the sample results can be incorrect or misleading. As a result, the ability to identify when a sample includes contributors having a high degree of allele sharing would substantially impact the underlying scientific assumptions that are made as well as improve the accuracy of conclusions that are drawn from the analyzed data.

BRIEF SUMMARY OF THE INVENTION

The present invention uses machine learning to probabilistically evaluate whether a DNA sample contains related individuals and/or unrelated individuals with high levels of alleles sharing. This approach provides a higher-confidence, more rapid analysis of the data, and enhanced decisional capabilities for the analysis of DNA mixtures. The machine learning algorithms used to implement the present invention may be selected and developed using training data that have been identified as directly relevant to the analysis of DNA samples containing relatives or non-relatives with high levels of allele sharing and drawn exclusively from mixtures of known contributors and proportions. The trained and validated machine learning algorithms may then developed to rapidly and probabilistically assess the presence of relatives in a DNA mixture.

More specifically, the present invention comprises a method of determining whether a sample of DNA contains related contributors, comprising the steps of receiving peak detection signals for a predetermined number of loci in a DNA sample, establishing from the peak detection signals a first set of peak detection data to be transformed and a second set of peak detection data to remain untransformed, transforming the first set of peak detection data using at least one of a plurality of transformation approaches, inputting the transformed first set of peak detection data and untransformed second set of peak detection data into a trained machine learning algorithm to produce a probability for each locus in the DNA sample that there were multiple, genetically related contributors. The plurality of transformation approaches may include: performing signal detection by determining an average baseline noise for each locus and then thresholding each locus with the average baseline noise for that locus; trimming the peak detection signals by [i] and any signals indicating slipped strand mispairing or sequencing errors and determining a ratio of a minimum trimmed signal and a baseline value; dividing a peak height for a bi-allelic gender determining marker by a total peak height of a multi-allelic gender specific marker and then by a number of contributors as determined according to a maximum allele count; determining a difference between a peak height for a female specific allele in a bi-allelic gender determining DNA marker and a total peak height for all alleles detected at a multi-allelic gender specific marker; dividing the difference between the peak height for the female specific allele in the bi-allelic gender determining DNA marker and the total peak height for all alleles detected at the multi-allelic gender specific marker by a total peak height for all alleles detected at the multi-allelic gender specific marker; determining an average signal threshold across all loci; determining a ratio of the locus with a maximum peak height over all loci to the locus with the minimum peak height over all loci; determining a ratio of the locus with a maximum peak area over all loci to the locus with the minimum peak area over all loci. The trained machine learning algorithm may considers allele-sharing when determining the probability that the DNA sample includes DNA from multiple contributors that are genetically related. The invention may also include determining a probability that there were multiple, genetically related contributors to the DNA sample based upon the probability for each locus in the DNA sample that there were multiple, genetically related contributors.

The present invention may also comprise a system for determining whether a sample of DNA contains related contributors that has a first module programmed to receive data representing peak detection signals for a predetermined number of loci in a DNA sample from a sequencing device, a second module programmed to establish from the peak detection signals a first set of peak detection data to be transformed and a second set of peak detection data to remain untransformed, a third module programmed to transform the first set of peak detection data using at least one of a plurality of transformation approaches, and a fourth module programmed to input the transformed first set of peak detection data and untransformed second set of peak detection data into a trained machine learning algorithm to produce a probability for each locus in the DNA sample that there were multiple, genetically related contributors.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a chart of exemplary allele sharing probabilities according to the present invention;

FIG. 2 is a chart of exemplary relative probabilities according to the present invention;

FIG. 4 is a table of results demonstrating the improvement to conventional analysis with the additional use of allele sharing probabilities determined according to the present invention.

DETAILED DESCRIPTION OF THE INVENTION

Figure 3:
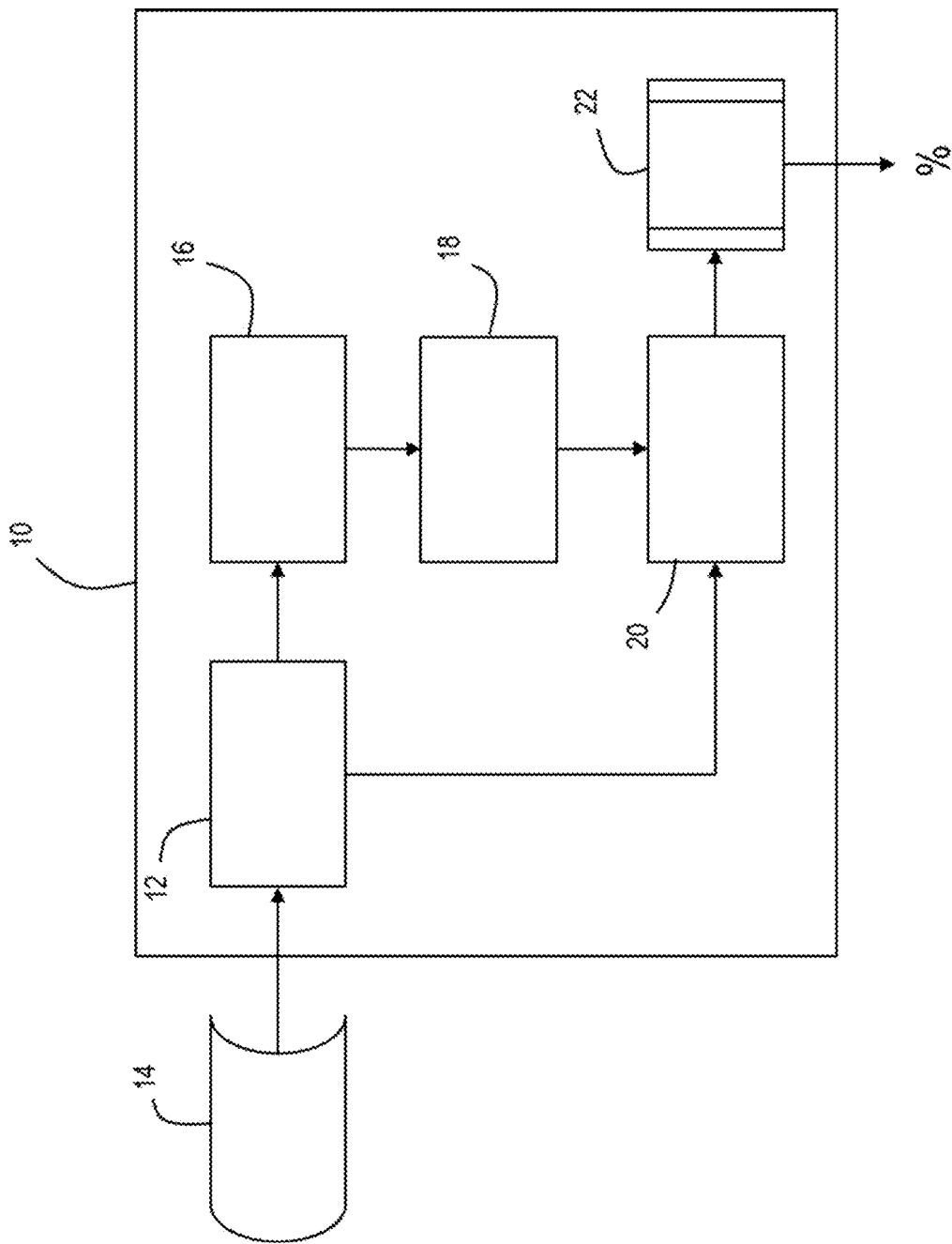
FIG. 3 is a schematic of a system for determining allele sharing probabilities according to the present invention.

Referring to the figures, wherein like numeral refer to like parts throughout, the present invention comprises a system and method for analyzing DNA sample data to determine whether the sample contains multiple contributors that have a high degree of allele sharing, such as contributors with familial relationships or contributors from isolated populations known to have high degrees of allele sharing. The present invention is configured to use conventional DNA sample data such as that output from peak detection or sequencing systems, including but not limited to Genemarker and Genemarker HID from SoftGenetics, Osiris (open-source), ArmedXpert (Niche Vision Forensics LLC), ForenSeq Universal Analysis software and Miseq/NextSeq/HiSeq Reporter (Illumina), Variant Reporter, NextGene, GeneMapper, GeneMapper IDX, Peak Scanner, Avadis, SeqScape, Ion Reporter, Sequencing Analysis Software, Converge Forensic Analysis Software (ThermoFisher Scientific), and ExactID (Batelle).

Data obtained from the peak detection or sequencing system are transformed and placed within a feature vector for input into a machine learning algorithm as described herein. The transformed data are coupled with untransformed data from the output of the peak detection or sequencing system to produce a unique feature vector that is optimized for use in predicting the degree of allele-sharing within a given DNA marker or if a mixed DNA sample is composed of genetically related individuals. The transformed data are critical to the function of the approach described herein as, in its absence, the resulting model will have significantly less predictive power.

The transformed features of the DNA sample data include, but are not limited to, the following aspects. A first transformation may be the use of a baseline detection tool to detect a signal. The signal detection tool is implemented per DNA locus, i.e., marker (within a sample). This tool averages the baseline noise surrounding a DNA locus of interest, calculates the standard deviation and applies a signal detection threshold to individual DNA loci within a sample. This method is dynamic across each instrument run, each sample, and each DNA locus/marker being analyzed. This approach differs from traditional analysis methods, for example, in the use of fragment analyses and that signal detection is a static value across all loci or loci labeled with the same fluorescent tag.

A second transformation may involve the number of signals being trimmed by a predetermined number, i, coupled with the number of signals removed due to slipped strand mispairing and/or sequencing errors. The ratio of the minimum signal after trimming by i is then determined, and the baseline value (sequence count or relative fluorescent unit–peak height) is calculated using i.

Another transformation may be a peak height or sequence count of a bi-allelic gender determining marker is divided by the total peak height or sequence count of a multi-allelic gender specific marker and then divided by the number of contributors as determined using the maximum allele count method.

A further transformation may be the difference of the (1) peak height or sequence count of the female specific allele in a bi-allelic gender determining DNA marker and (2) the total peak height or sequence count of all alleles is detected at the multi-allelic gender specific marker and then divided by the total peak height or sequence count of all alleles detected at the multi-allelic gender specific marker.

An additional transformation may be the determination of an average signal threshold as determined by i across all DNA markers labeled with the same fluorescent tag.

A further transformation may be the ratio of the allele with the maximum peak height or sequence count across the entire sample to the allele with the minimum peak height or sequence count across the entire sample is then determined. Although ratios are commonly used in the analysis of mixed DNA samples, these ratios are typically constrained to the ratio of individual alleles to one another within each locus and not in the manner described herein.

Yet another transformation may be the ratio of the allele with the maximum peak area across the entire sample and the allele with the minimum peak area across the entire sample is determined next and only made applicable to DNA fragment data. Once again, while ratios are commonly used in the analysis of mixed DNA samples, these ratios are typically constrained to the ratio of individual alleles to one another within each locus and are thus not used in the same manner as the present invention.

Thus, one or more these transformations may be used to prepare a transformed data set used to evaluate the DNA sample and determine the probability that there were genetically related contributors, as described herein.

The optimized feature vector containing the transformed data and the untransformed data is then used as input into a machine learning algorithm. The machine learning algorithm may be but is not limited to the following: an artificial Neural Network such as a multi-layer perceptron, a Support Vector Machine (SVM), decision trees such as C4.5, ensemble methods such as stacking, boosting and random forests, deep learning such as a Convolutional Neural Network (CNN), and clustering such as k-means. As many successful learning algorithms may be used, the present invention can make use of one or more learning algorithms. For example, multi-layer perceptrons (MLP) are a form of artificial neural network comprised of layers of nodes forming a directed graph. The initial layer of nodes, called the input layer, receives parameters used by the learning algorithm while the final layer of nodes, called the output layer, contains one node for every class that a sample could be classified. All other layers in a MLP are inner, "hidden" layers of nodes with nonlinear activation functions; these are modeled after the firing of biological neurons in the brain. A MLP using back propagation (Rumelhart et al. 1986) is arguably considered the basic, standard algorithm for classification via supervised machine learning, and in this project functions as a baseline for evaluating all other approaches.

Support vector machines (SVM) have a sound theoretical foundation originating in statistical learning theory (Vapnik 1998). For a linearly separable dataset in a two-class environment, SVM finds the classification function corresponding to the maximum margin of separation between a pair of hyperplanes that divide the two classes. If no hyperplane exists that can separate the two classes entirely, a "soft margin" method (Cortes & Vapnik 1995) finds a hyperplane that splits the examples as cleanly as possible while still maximizing the margin for cleanly split examples. The basic two-class environment can be extended to work with data-sets that can't be linearly separated and—importantly for this project—to incorporate additional classes (Crammer & Singer, 2002), allowing the algorithm to classify samples into all possible combinations of genetic contributors. While SVMs are widely regarded as computationally powerful, their main drawback has historically been their corresponding computational inefficiency. Recent approaches (Tsang et al. 2005) have largely resolved the issue, making this learner one of the more frequently tried classification algorithms.

Decision trees are a rule-based approach to classification and fit neatly with the project's aim to combine the computational power of machine-based learning with the expert knowledge found in more traditional forensic approaches. These traditional rule sets can be augmented using the Iterative Dichotomiser 3 algorithm (ID3) or one of its successors such as C4.5 (Quinlan 1993); such learning algorithms automatically generate a decision tree given an initial dataset. A C4.5-generated decision tree not only serves as a comparison to existing rule sets, but it may also suggest ways to improve those rule sets prior to their utilization by other machine learning algorithms such as MLP and SVM.

Stacking is an ensemble learning method (Dietterich 1997) that combines the predictions of multiple algorithms such as those described above. All "input algorithms" are trained, and then a logistic regression model is trained to classify using the other algorithms' classifications as inputs. Stacking often produces superior classification to what any of its component algorithms offer independently (Wolpert 1992). This project will evaluate multiple stacked combinations of algorithms from among the previously described five.

The present invention thus includes the configuration of one or more approaches for use with an unknown DNA sample. For configuration prior to use on an unknown sample, the machine learning algorithm may have been previously trained using a labeled data set for which the amount of allele-sharing or presence of relatives is already known, and a resulting model will would then have been produced that probabilistically characterizes the degree amount of allele-sharing. This optional allele-sharing model may be used to probabilistically evaluate subsequent, previously unseen DNA mixtures such as those obtained from the peak detection or sequencing system as described above.

The training data set is also used to train a second machine learning algorithm, which will have learned a second model that is specifically designed to estimate the probability that a mixed DNA sample contains related individuals, based on both untransformed and derived data from both the overall mixture and a given DNA marker. Because the allele-sharing model is an optional component of this invention, it is possible that the model described herein is the first model in the invention; subsequent steps are identical, regardless. Transformed data may include but are not limited to those described above as well as the allele-sharing probabilities obtained from the use of the algorithm on known data set. The machine learning algorithm may include but is not limited to those algorithms described above. The machine learning algorithm will have been trained using a known data set and a resulting model will have been produced that estimates the probability that a given DNA locus contains relatives. All conventional methods used to analyze genetic relatedness cannot be applied to unknown samples while the present invention can be used on unknown samples.

Data for an unknown mixed DNA sample, the transformed data, and the model determined above that outputs probabilities related to allele-sharing, are used as elements for a second feature vector to be used with the machine learning algorithm and resulting model to identify locus-specific probabilities of the presence of related individuals in the mixed DNA sample. These individual, locus-specific probabilities are the features that comprise the feature vector for a third, final machine learning algorithm specifically meant to estimate the probability that the mixture as a whole (as opposed to individual loci within the mixture) is comprised of one or more relatives based on probabilistic data from each DNA marker. The algorithm may be but is not limited to those algorithms described above. As before, the machine learning algorithm will have been trained using a known data set and a resulting model will have been produced that estimates the probability that a mixed DNA sample contains related individuals.

The probabilities that are obtained from the present invention may be used in downstream applications to ensure that the correct considerations are being made when attempting to: (i) predict the number of contributors in a DNA sample using methods such as the maximum allele count method, the PACE software or the NOCit software, (ii) computationally deconvolute or isolate the individual contributors of mixtures using software such as TrueAllele, STRmix or ArmedXpert; and/or (iii) inform the user as to the appropriate hypotheses to use (in STRmix, TrueAllele, Lab Retiever, LRmix, FST, GenoProof, likeLTD-R) when calculating the likelihood ratios as to the presence or absence of an individual within a mixed DNA samples. Thus, the present invention can improve the efficiency and accuracy of the conventional approaches to interpreting DNA sample data.

Referring to FIG. 3, the present invention may be implemented in a dedicated system 10 for determining whether a sample of DNA contains related contributors. System 10 includes a first module 12 programmed to receive data 14 representing peak detection signals for a predetermined number of loci in a DNA sample from a sequencing device. System 10 further includes a second module 16 programmed to establish from the peak detection signals a first set of peak detection data to be transformed and a second set of peak detection data to remain untransformed. System 10 additionally includes a third module 18 programmed to transform the first set of peak detection data using at least one of a plurality of transformation approaches. System 10 also includes a fourth module 20 programmed to input the transformed first set of peak detection data and untransformed second set of peak detection data into a trained machine learning algorithm 22 to produce a probability for each locus in the DNA sample that there were multiple, genetically related contributors. System 10 may be implemented using conventional desktop or laptop computers. For example, a computer having a dual core processing running at @ 2.4 GHz (i5 or i7 Intel processor or equivalent AMD) and 8 GB of RAM with sufficient storage in hard drive or solid state memory may be used to implement the programmed elements of the present invention.

The present invention thus considers information in a DNA sample analysis that has not be considered before, such as peak heights, peak height ratios, maximum peak heights, minimum peak heights, ratios of allele heights to one another, number of contributors using maximum allele count method, and quantitative measures of the amount of DNA contributed by the male and female organisms. A system programmed according to the present invention may thus be identify whether a DNA sample has contributors that are not readily identifiable based on the data obtained from the initial analytical instrument, including in circumstances where a human analyst would have difficulty interpreting and developing a conclusion as to the contributors to the sample. The system of the present invention is thus able to assign a probability to each sample that indicates the likelihood a sample contains relatives or un-related but highly similar individual organisms, and this probability may be used to improve the speed of downstream processing of the DNA sample data and well as to improve the accuracy of the identification of contributors to the sample.

Example

There is seen in FIG. 1, an exemplary chart identifying the probabilistic determination of allele sharing over various samples and allele sharing classes. FIG. 2 illustrates the probabilistic determination that the samples of FIG. 1 contain contributors that are generic relatives. The allele sharing results of FIG. 1 were obtained from a model developed using 1038 samples amplified and the 24-plex PowerPlex Fusion DNA amplification kit. This yielded 24,912 sample-locus instances. The model results are seen in Table 1 below:

TABLE 1

Random Forest Train Accuracy: 0.993
Random Forest Test Accuracy: 0.880

|   | precision | recall | f1-score | support |
|---|---|---|---|---|
| 0 | 0.94 | 0.94 | 0.94 | 2416 |
| 1 | 0.85 | 0.76 | 0.80 | 282 |
| 2 | 0.87 | 0.87 | 0.87 | 1393 |
| 3 | 0.78 | 0.75 | 0.77 | 569 |
| 4 | 0.82 | 0.86 | 0.84 | 911 |
| 5 | 0.87 | 0.88 | 0.88 | 712 |
| 6 | 0.91 | 0.84 | 0.87 | 197 |
|   | 0.88 | 0.88 | 0.88 | 6480 avg/total |

Confusion matrix

| Class | 0 1 2 3 4 5 6 |
|---|---|
| 0 | [2273 5 66 34 13 25 0] |
| 1 | [34 214 14 10 8 2 0] |
| 2 | [36 17 1212 48 72 6 2] |
| 3 | [43 13 40 428 34 8 3] |
| 4 | [17 3 39 20 785 40 7] |
| 5 | [23 0 15 7 35 627 5] |
| 6 | [4 0 0 2 16 10 165] |

The results of allele sharing output for three selected sample are seen in Table 2 below:

TABLE 2

| sample | locus | P(allele share) class 0 | P(allele share) class 1 | P(allele share) class 2 | P(allele share) class 3 | P(allele share) class 4 | P(allele share) class 5 | P(allele share) class 6 |
|---|---|---|---|---|---|---|---|---|
| Sample 1 | AMEL | 0.937105726 | 0.005772248 | 0.016794426 | 0.013303449 | 0.014027936 | 0.010625252 | 0.002370964 |
| Sample 1 | CSF1PO | 0.937101734 | 0.005772244 | 0.016797265 | 0.013303443 | 0.014027931 | 0.010626423 | 0.002370962 |
| Sample 1 | D10S1248 | 0.937105333 | 0.005772248 | 0.016794296 | 0.013303449 | 0.014027936 | 0.010625775 | 0.002370964 |
| Sample 1 | D12S391 | 0.010475735 | 0.005766409 | 0.016778998 | 0.013290625 | 0.014015194 | 0.937304761 | 0.002368278 |
| Sample 1 | D13S317 | 0.937105491 | 0.005772247 | 0.01679435 | 0.013303449 | 0.014027935 | 0.010625565 | 0.002370963 |
| Sample 1 | D16S539 | 0.937104052 | 0.00577225 | 0.016794507 | 0.013303455 | 0.014027943 | 0.010626829 | 0.002370964 |
| Sample 1 | D18S51 | 0.937105599 | 0.005772248 | 0.016794505 | 0.013303449 | 0.014027936 | 0.0106253 | 0.002370964 |
| Sample 1 | D19S433 | 0.937103799 | 0.005772245 | 0.016794729 | 0.013303444 | 0.014027931 | 0.01062689 | 0.002370962 |
| Sample 1 | D1S1656 | 0.937104591 | 0.005772247 | 0.016795525 | 0.013303445 | 0.014027931 | 0.010625299 | 0.002370963 |
| Sample 1 | D21S11 | 0.937105827 | 0.005772248 | 0.016794323 | 0.01330345 | 0.014027936 | 0.010625253 | 0.002370964 |
| Sample 1 | D22S1045 | 0.937015541 | 0.005772146 | 0.01679452 | 0.013303251 | 0.014027747 | 0.010715879 | 0.002370916 |
| Sample 1 | D2S1338 | 0.029880032 | 0.005732017 | 0.016700565 | 0.0132231 | 0.01395156 | 0.918160488 | 0.002352239 |
| Sample 1 | D2S441 | 0.937103138 | 0.005772244 | 0.01679535 | 0.013303442 | 0.014027929 | 0.010626935 | 0.002370962 |
| Sample 1 | D3S1358 | 0.937105279 | 0.005772247 | 0.0167947 | 0.013303449 | 0.014027935 | 0.010625426 | 0.002370964 |
| Sample 1 | D5S818 | 0.937105902 | 0.005772248 | 0.016794276 | 0.013303449 | 0.014027936 | 0.010625225 | 0.002370964 |
| Sample 1 | D7S820 | 0.937105978 | 0.005772248 | 0.016794207 | 0.01330345 | 0.014027936 | 0.010625217 | 0.002370964 |
| Sample 1 | D8S1179 | 0.937105449 | 0.005772247 | 0.016794544 | 0.013303448 | 0.014027935 | 0.010625414 | 0.002370963 |
| Sample 1 | DYS391 | 0.937104571 | 0.005772247 | 0.016794181 | 0.013303447 | 0.014027933 | 0.010626658 | 0.002370963 |
| Sample 1 | FGA | 0.937077581 | 0.005772216 | 0.016794461 | 0.013303387 | 0.014027877 | 0.01065353 | 0.002370949 |
| Sample 1 | PentaD | 0.937105571 | 0.005772248 | 0.016794298 | 0.013303451 | 0.014027937 | 0.010625531 | 0.002370964 |
| Sample 1 | PentaE | 0.937105669 | 0.005772247 | 0.016794241 | 0.013303449 | 0.014027936 | 0.010625494 | 0.002370964 |
| Sample 1 | TH01 | 0.937105942 | 0.005772248 | 0.016794246 | 0.01330345 | 0.014027936 | 0.010625215 | 0.002370964 |
| Sample 1 | TPOX | 0.937105994 | 0.005772248 | 0.016794186 | 0.01330345 | 0.014027936 | 0.010625222 | 0.002370964 |
| Sample 1 | vWA | 0.937105905 | 0.005772248 | 0.016794284 | 0.01330345 | 0.014027936 | 0.010625214 | 0.002370964 |
| Sample 2 | AMEL | 0.010402064 | 0.005721609 | 0.016847622 | 0.013194812 | 0.045566831 | 0.905915895 | 0.00235 1166 |
| Sample 2 | CSF1PO | 0.010595974 | 0.005827672 | 0.017614941 | 0.013424852 | 0.939373384 | 0.010769398 | 0.002393779 |
| Sample 2 | D10S1248 | 0.011903711 | 0.005891781 | 0.940917999 | 0.013599477 | 0.014418324 | 0.01084985 | 0.002418858 |
| Sample 2 | D12S391 | 0.08644171 | 0.006023336 | 0.863289106 | 0.014602291 | 0.01602575 | 0.011155499 | 0.002462308 |
| Sample 2 | D13S317 | 0.011011742 | 0.00588753 | 0.941913475 | 0.013577087 | 0.014350798 | 0.010842358 | 0.002417009 |
| Sample 2 | D16S539 | 0.01169087 | 0.005892132 | 0.940890793 | 0.013640779 | 0.014607463 | 0.010850177 | 0.002418785 |
| Sample 2 | D18S51 | 0.019435752 | 0.005986788 | 0.927334795 | 0.014243448 | 0.019411945 | 0.011132958 | 0.002454313 |
| Sample 2 | D19S433 | 0.010651526 | 0.00586207 | 0.021562781 | 0.01351652 | 0.900642058 | 0.045357211 | 0.002407832 |
| Sample 2 | D1S1656 | 0.011047405 | 0.005888798 | 0.941584573 | 0.013587637 | 0.014629281 | 0.01084478 | 0.002417525 |
| Sample 2 | D21S11 | 0.017241265 | 0.005926071 | 0.934001057 | 0.013686532 | 0.015797956 | 0.010914735 | 0.002432546 |
| Sample 2 | D22S1045 | 0.011123687 | 0.005759095 | 0.017738094 | 0.01327552 | 0.017539955 | 0.932198329 | 0.00236532 |
| Sample 2 | D2S1338 | 0.020583848 | 0.00593931 | 0.93143338 | 0.013815783 | 0.014870049 | 0.010921319 | 0.002436312 |
| Sample 2 | D2S441 | 0.936557235 | 0.005771233 | 0.017350258 | 0.013301521 | 0.014025855 | 0.010623433 | 0.002370465 |
| Sample 2 | D3S1358 | 0.010580568 | 0.005827367 | 0.017025993 | 0.013422511 | 0.939614836 | 0.011135102 | 0.002393623 |
| Sample 2 | D5S818 | 0.010799397 | 0.005784197 | 0.016930418 | 0.013340492 | 0.471110014 | 0.479656357 | 0.002379125 |
| Sample 2 | D7S820 | 0.01078154 | 0.005829567 | 0.017994157 | 0.013426855 | 0.938755824 | 0.010817353 | 0.002394703 |
| Sample 2 | D8S1179 | 0.936466253 | 0.005789566 | 0.017335868 | 0.01338831 | 0.014025955 | 0.010623488 | 0.00237056 |
| Sample 2 | DYS391 | 0.931210196 | 0.005776459 | 0.016847213 | 0.013316857 | 0.01495785 | 0.015518339 | 0.002373085 |
| Sample 2 | FGA | 0.285532395 | 0.006151008 | 0.66429149 | 0.014937652 | 0.015224573 | 0.011335561 | 0.002527321 |
| Sample 2 | PentaD | 0.93381325 | 0.006373406 | 0.018978126 | 0.013803471 | 0.0140336 | 0.010626559 | 0.002371587 |
| Sample 2 | PentaE | 0.936743228 | 0.005773127 | 0.017160082 | 0.013302278 | 0.014026585 | 0.010624055 | 0.002370644 |
| Sample 2 | TH01 | 0.010622401 | 0.005842629 | 0.017949216 | 0.01351648 | 0.921526509 | 0.028142768 | 0.002399997 |
| Sample 2 | TPOX | 0.037601387 | 0.006269875 | 0.018087694 | 0.014298787 | 0.894607268 | 0.026535849 | 0.002599141 |

TABLE 2-continued

| sample | locus | P(allele share) class 0 | P(allele share) class 1 | P(allele share) class 2 | P(allele share) class 3 | P(allele share) class 4 | P(allele share) class 5 | P(allele share) class 6 |
|---|---|---|---|---|---|---|---|---|
| Sample 2 | vWA | 0.026302036 | 0.005976615 | 0.923943988 | 0.014083785 | 0.016236802 | 0.01100152 | 0.002455254 |
| Sample 3 | AMEL | 0.010587956 | 0.005831466 | 0.017051018 | 0.013431674 | 0.937867876 | 0.012793026 | 0.002436984 |
| Sample 3 | CSF1PO | 0.014334598 | 0.007926507 | 0.272012024 | 0.018800135 | 0.603798557 | 0.079900149 | 0.003228029 |
| Sample 3 | D10S1248 | 0.934861812 | 0.005778976 | 0.018571583 | 0.013777043 | 0.014021198 | 0.010619715 | 0.002369674 |
| Sample 3 | D12S391 | 0.011359227 | 0.005893369 | 0.940727898 | 0.01391562 | 0.014724671 | 0.010960301 | 0.002418913 |
| Sample 3 | D13S317 | 0.012437439 | 0.005906364 | 0.940197926 | 0.013612423 | 0.014474065 | 0.01095165 | 0.002420132 |
| Sample 3 | D16S539 | 0.012620698 | 0.006812776 | 0.228900164 | 0.016446031 | 0.35603211 | 0.376390077 | 0.002798144 |
| Sample 3 | D18S51 | 0.787926 | 0.075840894 | 0.078174584 | 0.02036216 | 0.018557195 | 0.016194518 | 0.002944649 |
| Sample 3 | D19S433 | 0.011487451 | 0.006389094 | 0.450798351 | 0.014553964 | 0.499907837 | 0.014227225 | 0.002636078 |
| Sample 3 | D1S1656 | 0.013042359 | 0.005912928 | 0.936258812 | 0.013667845 | 0.017670142 | 0.011021073 | 0.002426841 |
| Sample 3 | D21S11 | 0.916179962 | 0.018644923 | 0.022456395 | 0.015191832 | 0.014274438 | 0.010824878 | 0.002427572 |
| Sample 3 | D22S1045 | 0.01265859 | 0.005898875 | 0.939670792 | 0.014087368 | 0.014401191 | 0.010862143 | 0.00242104 |
| Sample 3 | D2S1338 | 0.010788921 | 0.006637422 | 0.024763259 | 0.016813061 | 0.924599036 | 0.013416352 | 0.002981948 |
| Sample 3 | D2S441 | 0.936517324 | 0.005774097 | 0.01731664 | 0.01337212 | 0.014025843 | 0.010623451 | 0.002370526 |
| Sample 3 | D3S1358 | 0.010601895 | 0.005842733 | 0.017139759 | 0.013449672 | 0.547269175 | 0.403288568 | 0.002408197 |
| Sample 3 | D5S818 | 0.015530841 | 0.008639271 | 0.497288984 | 0.019764175 | 0.183367802 | 0.271546296 | 0.003862631 |
| Sample 3 | D7S820 | 0.011725458 | 0.006002179 | 0.932035265 | 0.014651083 | 0.019126411 | 0.013937021 | 0.002522583 |
| Sample 3 | D8S1179 | 0.011201727 | 0.006231117 | 0.028139552 | 0.014401022 | 0.274269006 | 0.663166157 | 0.002591421 |
| Sample 3 | DYS391 | 0.911728422 | 0.005788501 | 0.016880318 | 0.013356062 | 0.01449416 | 0.03537326 | 0.002379276 |
| Sample 3 | FGA | 0.011014614 | 0.005888581 | 0.941696094 | 0.013707955 | 0.014413809 | 0.010861688 | 0.00241726 |
| Sample 3 | PentaD | 0.31857006 | 0.124519902 | 0.470969534 | 0.046595504 | 0.019403863 | 0.016839526 | 0.00310161 |
| Sample 3 | PentaE | 0.935981745 | 0.005811533 | 0.017695587 | 0.013493867 | 0.014024532 | 0.010622401 | 0.002370336 |
| Sample 3 | TH01 | 0.01059474 | 0.005835759 | 0.018667099 | 0.013490203 | 0.935985285 | 0.01299805 | 0.002428865 |
| Sample 3 | TPOX | 0.01285908 | 0.006995324 | 0.048360653 | 0.016403589 | 0.180492465 | 0.730717189 | 0.004171699 |
| Sample 3 | vWA | 0.930130634 | 0.005895954 | 0.021874286 | 0.015097547 | 0.014015123 | 0.010617543 | 0.002368914 |

For the genetic relative prediction of FIG. 2, the models were developed using 1220 samples amplified using the 24-plex PowerPlex Fusion DNA amplification kit. This yielded 29,280 sample-locus instances. The model results are seen in Table 3 below:

TABLE 3

Relatives no weighting
MLP Train Accuracy: 0.995
MLP Test Accuracy: 0.963

|  | precision | recall | f1-score | support |
|---|---|---|---|---|
| No Rel | 0.98 | 0.98 | 0.98 | 6480 |
| Rel | 0.72 | 0.71 | 0.71 | 456 |
| avg/total | 0.96 | 0.96 | 0.96 | 6936 |

Confusion matrix

|  | NoRel | Rel |
|---|---|---|
| NoRel | [6356 | 124] |
| Rel | [134 | 322] |

Relatives weighted using Probability of Identity
MLP Train Accuracy: 1.000
MLP Test Accuracy: 0.969

|  | precision | recall | f1-score | support |
|---|---|---|---|---|
| NoRel | 0.99 | 0.98 | 0.98 | 270 |
| Rel | 0.73 | 0.84 | 0.78 | 19 |
| avg/total | 0.97 | 0.97 | 0.97 | 289 |

Confusion matrix

|  | NoRel | Rel |
|---|---|---|
| NoRel | [264 | 6] |
| Rel | [3 | 16] |

The genetic relative prediction results from three selected samples are seen in Table 4 below:

TABLE 4

| sample | prob_relatives |
|---|---|
| Sample 1 | 0.991191 |
| Sample 2 | 0.002182 |
| Sample 3 | 0.003399 |

The present invention may be used to improve the performance of contributor estimation between 1.1- and 212-fold. The mean percent improvement in probability of the correct number of contributors is 7.9%. Three of the sample probabilities were improved by the present invention, but because the initial correct probabilities were already very close to 1.0 the improvements brought about by the present invention were, as a percentage, smaller. The present invention also improved the accuracy of PACE in 12 of 14 samples (85%), thus having a significant impact on the overall results. It is critical to note that, in the two samples that were not improved, both three-contributor samples with siblings were highly complex with high levels of allele sharing and the differences in the returned probabilities are negligible relative to the interpretation, i.e., the probabilities are below 15%. Evidence establishing the improved accuracy of contributor determination is seen in FIG. 4.

The use of the present invention also enables the probabilities to become more informative. For example, without the use of the present invention, analysis using Probabilistic Assessment for Contributor Estimate (PACE) incorrectly predicts the NOC for Sample No. 1 with a two-contributor probability of 0.69 and estimates only a 0.27 probability for the correct class (three-contributor). When using the output of the present invention, PACE returns a two-contributor probability of 0.55 and a three-contributor probability of 0.40. This could certainly cause the interpretation to be deemed inconclusive, but the use of the present invention otherwise prevents what is a clearly incorrect classification for an unknown sample. Moreover, the performance of the present invention is capable of being improved with the use of an increased number of training samples. In the present example of the present invention, only 112 relative-containing mixtures were used, 97 for training and 15 for testing.

A system according to the present invention may thus comprise a processor that is programmed to implement the approach described above. The processor can comprise, for example, a general purpose processor, an application specific processor, or any other processor suitable for carrying out the processing steps as described or otherwise envisioned herein. According to an embodiment, the processor may be a combination of two or more processors. The processor may be local or remote from one or more of the other components. For example, the processor might be located within a lab, within a facility comprise multiple labs, or at a central location that services multiple facilities. According to another embodiment, the processor may be offered via a software as a service. One of ordinary skill will appreciate that non-transitory storage medium may be implemented as multiple different storage mediums, which may all be local, may be remote (e.g., in the cloud), or some combination of the two.

The processor comprises or is in communication with a non-transitory storage medium. Database may be any storage medium suitable for storing program code for executed by the processor to carry out any one of the steps described or otherwise envisioned herein. Non-transitory storage medium may be comprised of primary memory, secondary memory, and/or a combination thereof. As described in greater detail herein, the database may also comprise stored data to facilitate the analysis, characterization, and/or identification of the DNA in the sample.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. A method of determining whether a sample of DNA contains related contributors, comprising the steps of:
receiving peak detection signals for a predetermined number of loci in a DNA sample;
establishing from the peak detection signals a first set of peak detection data to be transformed and a second set of peak detection data to remain untransformed;
transforming the first set of peak detection data using at least one of a plurality of transformation approaches;
inputting the transformed first set of peak detection data and untransformed second set of peak detection data into a trained machine learning algorithm to produce a probability for each locus in the DNA sample that there were multiple, genetically related contributors.

2. The method of claim 1, wherein the step of transforming the first set of peak detection data using at least one of the plurality of transformation approaches includes the step of performing signal detection by determining an average baseline noise for each locus and then thresholding each locus with the average baseline noise for that locus.

3. The method of claim 1, wherein the step of transforming the first set of peak detection data using at least one of the plurality of transformation approaches includes the step of trimming the peak detection signals by [i] and any signals indicating slipped strand mispairing or sequencing errors.

4. The method of claim 3, wherein the step of transforming the first set of peak detection data using at least one of the plurality of transformation approaches includes the step of determining a ratio of a minimum trimmed signal and a baseline value.

5. The method of claim 1, wherein the step of transforming the first set of peak detection data using at least one of the plurality of transformation approaches includes the step of dividing a peak height for a bi-allelic gender determining marker by a total peak height of a multi-allelic gender specific marker and then by a number of contributors as determined according to a maximum allele count.

6. The method of claim 1, wherein the step of transforming the first set of peak detection data using at least one of the plurality of transformation approaches includes the step of determining a difference between a peak height for a female specific allele in a bi-allelic gender determining DNA marker and a total peak height for all alleles detected at a multi-allelic gender specific marker.

7. The method of claim 6, wherein the step of transforming the first set of peak detection data using at least one of the plurality of transformation approaches further includes the step of dividing the difference between the peak height for the female specific allele in the bi-allelic gender determining DNA marker and the total peak height for all alleles detected at the multi-allelic gender specific marker by a total peak height for all alleles detected at the multi-allelic gender specific marker.

8. The method of claim 1, wherein the step of transforming the first set of peak detection data using at least one of the plurality of transformation approaches includes the step of determining an average signal threshold across all loci.

9. The method of claim 1, wherein the step of transforming the first set of peak detection data using at least one of the plurality of transformation approaches includes the step of determining a ratio of the locus with a maximum peak height over all loci to the locus with the minimum peak height over all loci.

10. The method of claim 1, wherein the step of transforming the first set of peak detection data using at least one of the plurality of transformation approaches includes the step of determining a ratio of the locus with a maximum peak area over all loci to the locus with the minimum peak area over all loci.

11. The method of claim 1, wherein the trained machine learning algorithm considers allele-sharing when determining the probability that the DNA sample includes DNA from multiple contributors that are genetically related.

12. The method of claim 1, further comprising the step of determining a probability that there were multiple, genetically related contributors to the DNA sample based upon the probability for each locus in the DNA sample that there were multiple, genetically related contributors.

13. A system for determining whether a sample of DNA contains related contributors, comprising:
a computer processor programmed to include a first module configured to receive data representing peak detection signals for a predetermined number of loci in a DNA sample from a sequencing device;
wherein the processor is further programmed to include a second module configured to establish from the peak detection signals a first set of peak detection data to be transformed and a second set of peak detection data to remain untransformed;
wherein the processor is further programmed to include a third module configured to transform the first set of peak detection data using at least one of a plurality of transformation approaches;
wherein the processor is further programmed to include a fourth module configured to input the transformed first set of peak detection data and untransformed second set of peak detection data into a trained machine learning algorithm to produce a probability for each locus in the DNA sample that there were multiple, genetically related contributors.

14. The system of claim 1, wherein the plurality of transformation approaches used by third module include performing signal detection by determining an average baseline noise for each locus and then thresholding each locus with the average baseline noise for that locus, trimming the peak detection signals by [i] and any signals indicating slipped strand mispairing or sequencing errors, dividing a peak height for a bi-allelic gender determining marker by a total peak height of a multi-allelic gender specific marker and then by a number of contributors as determined according to a maximum allele count, determining a difference between a peak height for a female specific allele in a bi-allelic gender determining DNA marker and a total peak height for all alleles detected at a multi-allelic gender specific marker.

15. The system of claim 14, wherein transforming the first set of peak detection data using at least one of the plurality of transformation approaches comprises determining a ratio of a minimum trimmed signal and a baseline value.

16. The system of claim 6, wherein transforming the first set of peak detection data using at least one of the plurality of transformation approaches comprises dividing the difference between the peak height for the female specific allele in the bi-allelic gender determining DNA marker and the total peak height for all alleles detected at the multi-allelic gender specific marker by a total peak height for all alleles detected at the multi-allelic gender specific marker.

17. The system of claim 1, wherein the trained machine learning algorithm includes consideration of allele-sharing when determining the probability that the DNA sample includes DNA from multiple contributors that are genetically related.

18. The system of claim 1, wherein the processor is further programmed to include a fifth module configured to determine a probability that there were multiple, genetically related contributors to the DNA sample based upon the probability for each locus in the DNA sample that there were multiple, genetically related contributors.

* * * * *